United States Patent
Pelissier et al.

(10) Patent No.: US 10,405,836 B2
(45) Date of Patent: Sep. 10, 2019

(54) SPECKLE REDUCTION AND COMPRESSION IMPROVEMENT OF ULTRASOUND IMAGES

(71) Applicant: Clarius Mobile Health Corp., Burnaby (CA)

(72) Inventors: Laurent Pelissier, North Vancouver (CA); Kris Dickie, Vancouver (CA); Narges Afsham, Coquitlam (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 645 days.

(21) Appl. No.: 14/949,708

(22) Filed: Nov. 23, 2015

(65) Prior Publication Data
US 2017/0143313 A1 May 25, 2017

(51) Int. Cl.
| | |
|---|---|
| *A61B 8/00* | (2006.01) |
| *A61B 8/08* | (2006.01) |
| *G01S 7/52* | (2006.01) |
| *G01S 15/89* | (2006.01) |

(52) U.S. Cl.
CPC ............ *A61B 8/565* (2013.01); *A61B 8/4483* (2013.01); *A61B 8/461* (2013.01); *A61B 8/5207* (2013.01); *A61B 8/5246* (2013.01); *A61B 8/5269* (2013.01); *A61B 8/54* (2013.01); *G01S 7/5208* (2013.01); *G01S 7/52034* (2013.01); *G01S 7/52077* (2013.01); *G01S 7/52098* (2013.01); *G01S 15/8915* (2013.01)

(58) Field of Classification Search
None
See application file for complete search history.

(56) References Cited

U.S. PATENT DOCUMENTS

| | | |
|---|---|---|
| 4,747,150 A | 5/1988 | Knutsson et al. |
| 4,747,151 A | 5/1988 | Knutsson et al. |
| 4,747,152 A | 5/1988 | Knutsson et al. |
| 5,570,691 A | 11/1996 | Wright et al. |
| 5,594,767 A | 1/1997 | Hsieh |
| 5,602,934 A | 2/1997 | Li et al. |

(Continued)

FOREIGN PATENT DOCUMENTS

| | | |
|---|---|---|
| WO | 2009065441 A1 | 5/2009 |
| WO | 2012066568 A1 | 5/2012 |

OTHER PUBLICATIONS

Rui et al., "Adaptive Filter for Speckle Reduction with Feature Preservation in Medical Ultrasound Images", 10th Intl. Conf. on Control, Automation, Robotics and Vision, Hanoi, Vietnam, Dec. 17-20, 2008, pp. 1787-1792.*

(Continued)

*Primary Examiner* — Katherine L Fernandez
(74) *Attorney, Agent, or Firm* — Julian Ho

(57) ABSTRACT

An apparatus and method for generating high quality, high frame rate images in a handheld or hand-carried ultrasonic imaging machine. The apparatus includes an image enhancer to reduce speckle noise and improve the compressibility of the resulting image. This approach reduces the required hardware and power consumption to satisfy the physical space, power, and limited processing power of a handheld probe and enables high quality images to be transmitted efficiently over low-bandwidth connections.

19 Claims, 7 Drawing Sheets

(56) References Cited

U.S. PATENT DOCUMENTS

| | | | |
|---|---|---|---|
| 5,961,461 A * | 10/1999 | Mo ........................ | G06T 5/20 600/443 |
| 6,349,143 B1 * | 2/2002 | Hastings ............ | G01S 7/52034 382/128 |
| 7,071,947 B1 | 7/2006 | Papakipos et al. | |
| 7,809,178 B2 | 10/2010 | Spies et al. | |
| 8,414,493 B2 | 4/2013 | Derby, Jr. | |
| 2005/0053305 A1 | 3/2005 | Li et al. | |
| 2005/0054921 A1 * | 3/2005 | Katsman ............... | G01S 7/003 600/437 |
| 2005/0228279 A1 | 10/2005 | Ustuner et al. | |
| 2007/0242567 A1 | 10/2007 | Daft et al. | |
| 2008/0250870 A1 | 10/2008 | Rhodes | |
| 2010/0166063 A1 * | 7/2010 | Perlman ............ | H04N 21/2662 375/240.07 |
| 2012/0019690 A1 * | 1/2012 | Stirling-Gallacher ...................... | G01S 7/2923 348/241 |
| 2012/0092533 A1 | 4/2012 | Komori | |
| 2012/0108973 A1 | 5/2012 | Osumi | |
| 2013/0243296 A1 | 9/2013 | Nandi et al. | |
| 2014/0195577 A1 * | 7/2014 | Nikitin ................. | H03H 7/0153 708/304 |
| 2014/0276069 A1 | 9/2014 | Amble et al. | |
| 2014/0357993 A1 * | 12/2014 | Hiriyannaiah ......... | A61B 8/565 600/437 |
| 2014/0358005 A1 | 12/2014 | Hiriyannaiah | |
| 2015/0092838 A1 | 4/2015 | Hiriyannaiah et al. | |
| 2015/0094591 A1 | 4/2015 | Hiriyannaiah | |

OTHER PUBLICATIONS

Stuijk, "Design and implementation of a JPEG decoder", Practical training report, Faculty of Electrical Engineering of the Eindhoven University of Technology, Dec. 2001.*

Westin et al., "Adaptive Image Filtering", Handbook of Medical Image Processing and Analysis, edited by Isaac Bankman, 2008, pp. 19-31.*

Gupta et al., "Despeckling of Medical Ultrasound Images Using Data and Rate Adaptive Lossy Compression", IEEE Transactions on Medical Imaging, vol. 24, No. 6, Jun. 2005, pp. 743-754.*

Wei et al., "Simultaneous speckle reduction and data compression using best wavelet packet bases with application to SAR based ATD/R", Proceedings of SPIE, Mathematical Imaging: Wavelet Applications for Dual use, Apr. 17-21, 1995, Orlando, FL, pp. 1-11.*

Lau, C. et al. (2000). "MPEG-4 Coding of Ultrasound Sequences", Department of Bioengineering and Electrical Engineering, University of Washington, in Proceedings of the SPIE, Medical Imaging 2000 Display Conference vol. 3976, 573-579.

Abstract of Cabral, J.E., Tinker, D.T., and Kim, Y. (1998). "Compression for pre-scan-converted ultrasound sequences", in Proceedings of the SPIE, Medical Imaging 1998 Image Display vol. 3335, 378.

Abstract of Miri, R., Setarehdan, S.K., and Maralani, P.J. (2003). "Ultrasound Data Compression in a Tele-Ultrasound System", Journal (216) Biomedical Engineering 2003.

Abstract of Wu, W., Acton, S.T., and Lach, J., "Real-Time Processing of Ultrasound Images with Speckle Reducing Anisotropic Diffusion", published in Fortieth Asilomar Conference on Signals, Systems and Computers, 2006. ACSSC 06. Date of Conference: Oct. 29-Nov. 1, 2006.

Yu, Y. and Acton, S.T., "Speckle Reducing Anisotropic Diffusion", in IEEE Transactions on Image Processing 11 (11) 2002: 1260-1270.

Jensen, A.F.C. (2003). "The General Flow-Adaptive Filter with Applications to Ultrasound Image Sequences", Department of Informatics, University of Oslo.

Aja-Fernandez, S. et al., "Tensors in Image Processing and Computer Vision", Advances in Pattern Recognition, Springer-Verlag London Limited 2009.

Benzarti, F. and Amiri, H., "Speckle Noise Reduction in Medical Ultrasound Images", International Journal of Computer Science Issues 9 (2) 2012.

Contextvision. "Image Enhancement Packages Optimized for Different Clinical Applications", Product Description US Plusview Packages, 2D Image Enhancement for Ultrasound, Dec. 2014. Available at http://www.contextvision.com/wordpress/wp-content/uploads/2014/12/ContextVision-US-PLUSView.pdf, last accessed Feb. 28, 2017.

Sapheneia. "Clarity OEM Ultrasound Adavantages", Image Optimization Software Improving Diagnostic Confidence, Dec. 2014. Available at http://sapheneia.com/wp-content/uploads/2014/12/Sapheneia-Ultrasound-OEM-flyer.pdf, last accessed Feb. 28, 2017.

Mathworks. Publication date unknown. Available at http://www.mathworks.com/help/images/ref/edge.html?s_tid=gn_loc_drop, last accessed Feb. 28, 2017.

Contextvision. "The GOP Technology". Publication date unknown. Available at http://www.contextvision.com/our-technology/the-gop-pyramid/, last accessed Mar. 2, 2017.

* cited by examiner

SPECKLE REDUCTION AND COMPRESSION IMPROVEMENT OF ULTRASOUND IMAGES

FIELD

This invention relates to ultrasound imaging systems. Particular embodiments provide ultrasound imaging machines and related methods. Some embodiments process ultrasound images in ways that facilitate transfer of the ultrasound images while maintaining image quality.

BACKGROUND

Ultrasound is a useful, non-invasive imaging method used for diagnosing a variety of conditions. Historically, ultrasound machines were large, expensive machines used only in radiology departments by high trained specialists. Various attempts have been made to reduce the size and cost of medical ultrasound systems while maintaining high image quality. There is a general desire to enable ultrasound to be more portable, and used at the point-of-care by more users.

One of the main factors that negatively affects ultrasound image quality is a type of inherent noise called speckle. Speckle reduces resolution and image contrast, decreasing diagnostic accuracy.

A variety of methods exist to reduce the impact of speckle, either by reducing how much speckle is created in the first place or by employing image processing to remove speckle from images. The goal of speckle reduction is to remove the speckle to increase image quality without losing too much useful diagnostic information. Smoothing can remove speckle, but also affects fine details and edges. There are better speckle reduction techniques. However, these typically require significant processing power and can therefore be performed only using hardware that provides significant computer resources.

There remains a need for apparatus and methods capable of producing good quality ultrasound images. The inventors have realized that there is a particular need for small, portable ultrasound devices which can provide such images.

SUMMARY

This invention has a number of different aspects that have synergy when combined but are also capable of application individually and/or in subcombinations. Some aspects provide methods for speckle reduction suitable for application in portable battery-powered ultrasound imaging devices. In some embodiments, the speckle reduction is performed on a portable device before speckle-reduced images are transmitted to another device by a data link. The inventors have found that combination of speckle reduction with data compression can significantly reduce the volume of data required to transmit the image. This, in turn facilitates real-time transmission of ultrasound images over limited-bandwidth data connections while maintaining acceptable image quality.

One example aspect provides a method for ultrasound imaging, the method comprising:
acquiring ultrasound image data;
performing signal processing of the ultrasound image data to yield ultrasound images;
performing image processing on the ultrasound images wherein the image processing comprises performing a speckle-reduction algorithm;
compressing the processed ultrasound images;
transmitting the compressed ultrasound images to a display device
performing scan conversion at the display device; and
displaying the scan-converted ultrasound images at the display device.

Another aspect provides a ultrasonic imaging system comprising an ultrasonic imaging machine configured to acquire ultrasound image data from a patient and transmit the data to a user interface using a low bandwidth connection. The ultrasound imaging machine is configured to perform methods as described herein.

The methods and systems described herein may increase the quality and framerate of ultrasound images, helping clinicians make better diagnostic decisions.

Further aspects and example embodiments are illustrated accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1A:
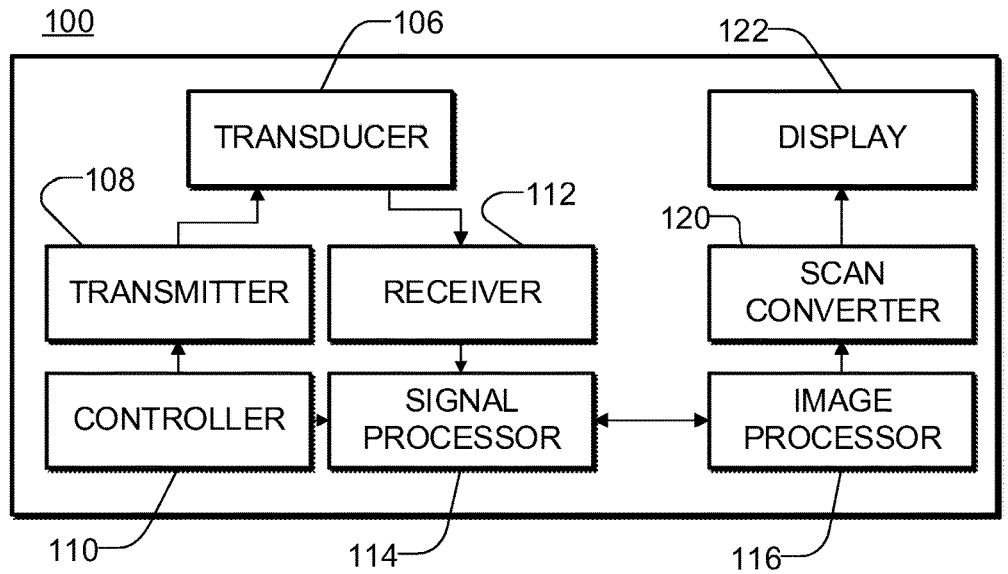
FIG. 1A is a schematic diagram of a prior art ultrasound imaging system.

FIG. 1 is a block diagram illustrating major functional parts of a typical ultrasound machine 100. Machine 100 includes a transducer array 106 that comprises a plurality of transducer elements. The transducer elements are operable to both transmit and receive ultrasound energy. When energized by transmitter 108, the transducer elements produce a burst of ultrasonic energy.

The ultrasound energy produced by transducer array 106 is directed towards a body region of a patient containing a volume of interest. Some of the ultrasound energy is reflected back to transducer array 106 by structures within the volume of interest as echo signals. Transducer array 106 receives the echo signals and converts the received ultrasound energy into analog electrical signals which are processed by receiver 112 into ultrasound beams. This processing is often called "beamforming". The ultrasound beams are then combined to form an image in signal processor 114. The ultrasound image is further processed in image processor 116, before being scan converted at scan converter 120 and output to a display 120. Images displayed on display 120 may, for example, be B mode images.

Figure 1B:
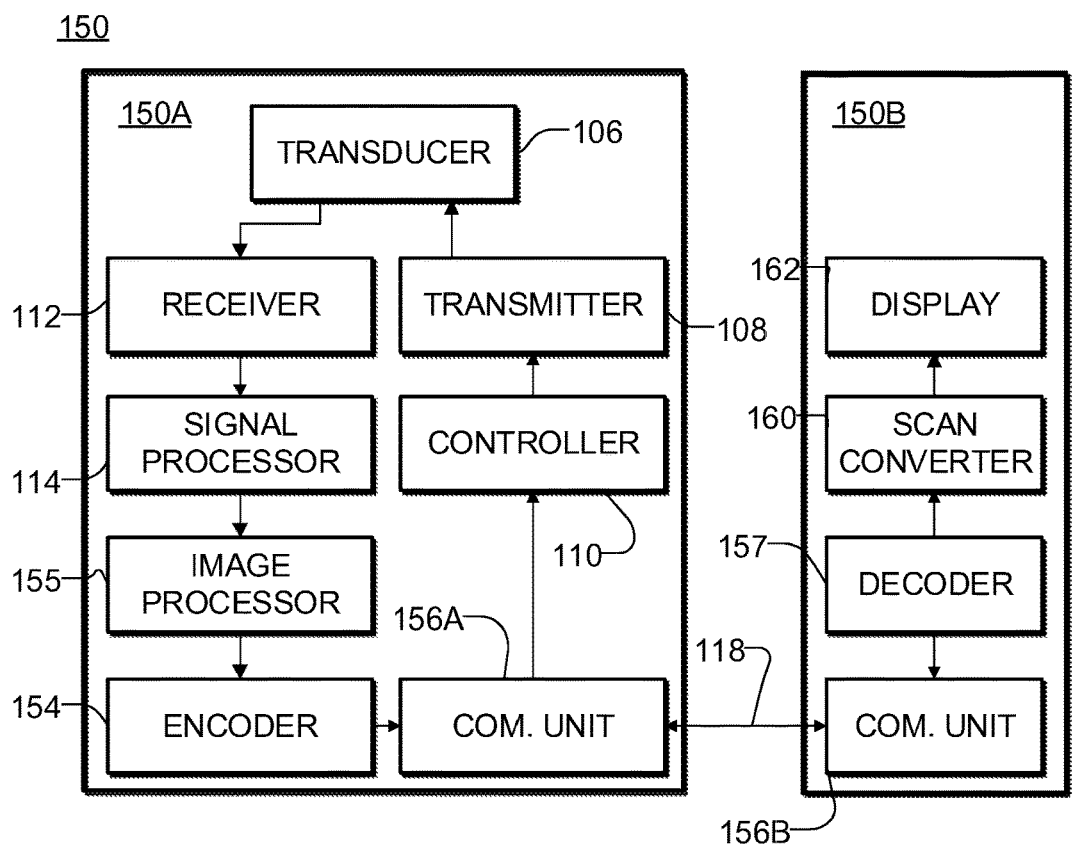
FIG. 1B is a schematic diagram of an ultrasound imaging system according to an example embodiment of the present disclosure.

FIG. 1B illustrates an ultrasonic imaging system 150 in accordance with some embodiments of the present invention. System 150 comprises an ultrasound imaging machine 150A and a separate display device 150B that are connected via a communication link 118. In some embodiments link 118 is a wireless data link. Link 118 may be established between wireless transceivers (e.g. communication units 156A and 156B respectively of ultrasound imaging machine 150A and display device 150B). In some embodiments, display device 150B is a multi-use device such as a smart phone, tablet, portable computer, or the like that has a display which may be used for displaying ultrasound images as well as for other purposes.

Ultrasound machine 150A includes functionality for acquiring ultrasound image data from a patient. In the illustrated embodiment this functionality is provided by a transducer 106 which is driven by a transmitter 108 to transmit ultrasound signals into a patient under control of a controller 110. Echo signals are received at transducer 106 detected and beamformed by receiver 112 and processed by signal processor 114. The basic functionality for acquiring ultrasound images may be provided using any suitable hardware including arrangements that are known in the prior art and arrangements that may be discovered in future.

In ultrasound imaging machine 150A, image processing is performed on ultrasound images from signal processor 114 by an image processor 155. The resulting processed images are passed to an encoder 154 which receives an ultrasound image from image processor 155 and applies a compression algorithm to reduce the size of the ultrasound image to more efficiently transmit via communication link 118 to display device 150B. The ultrasound image received by device 150B is decoded by decoder 157 before scan conversion is performed by scan converter 160 and the resulting image is displayed on display 162.

Communication link 118 may comprise a wired or wireless connection and may comprise more than one communication protocol. Communication link 118 may have a limited bandwidth. For example, a preliminary connection may be a Bluetooth™ low energy (BLE) connection and a primary connection may be a Wi-Fi connection. In other examples, one or more of the following protocols may be used: wireless local area network (LAN), Bluetooth, ZigBee™, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), radio frequency (RF) communication, infrared (IR) communication and the like. In some cases it may be desirable to limit the bandwidth used by a device 150A to transmit ultrasound image data across communication link 118 even if communication link 118 could provide a higher bandwidth to the transmissions from device 150A. For example, communication link 118 may be shared by a significant number of devices 150A and possibly other devices as well and it may be desirable to leave bandwidth available for other purposes.

The inventors have found that performing speckle reduction at device 150A prior to performing data compression at encoder 154 can significantly reduce the volume of data to be transmitted over communication link 118 to device 150B while preserving image quality. In some embodiments speckle reduction or speckle reduction and compression are controlled to limit the bandwidth required for transmission of the ultrasound data to be within an allowed bandwidth while preserving image quality of transmitted ultrasound images.

Speckle Reduction and Compression

Figure 2:
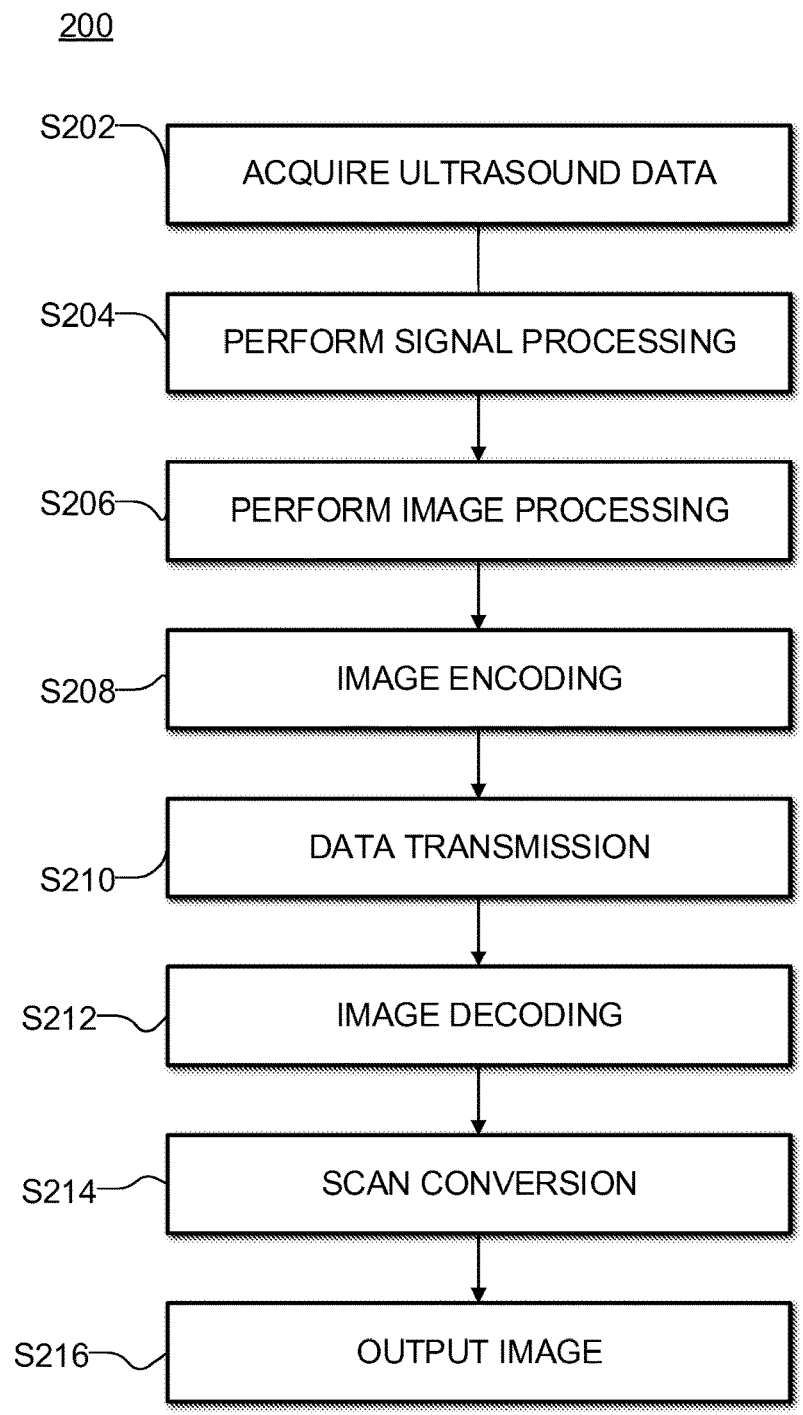
FIG. 2 is a flow chart illustrating and image enhancement and compression method that may be performed by an ultrasound imaging machine according to an example embodiment of the present disclosure.

FIG. 2 is a flowchart illustrating a method 200 that may be performed by system 150 according to an embodiment of the present disclosure.

In operation S202, ultrasound data is acquired. This operation may include numerous different steps, including, but not limited to: transmit beamforming, amplification, analog to digital conversion, and receive beamforming. A wide range of suitable methods for acquiring ultrasound data are known to those of skill in the art.

In operation S204, the ultrasound data is processed into an ultrasound image. Signal processing may, for example, include the steps of FIR filtering, envelope detection, and log compression.

In operation S206, the ultrasound image is processed to reduce speckle noise. As discussed herein, processing in operation S206 may also improve compressibility. The output of operation S206 is a speckle-reduced image.

In operation S208, the speckle-reduced ultrasound image is encoded. The encoding yields an encoded image. The encoded image is preferably reduced in size (compressed) relative to the speckle-reduced ultrasound image. Encoding may comprise applying one or more data compression algorithms.

In operation S210, the ultrasound image is transmitted to the multi-use display device 150B.

In operation S212, the ultrasound image is decoded.

In operation S214, the ultrasound image is scan converted.

In operation S216 the ultrasound image is displayed.

Figure 3:
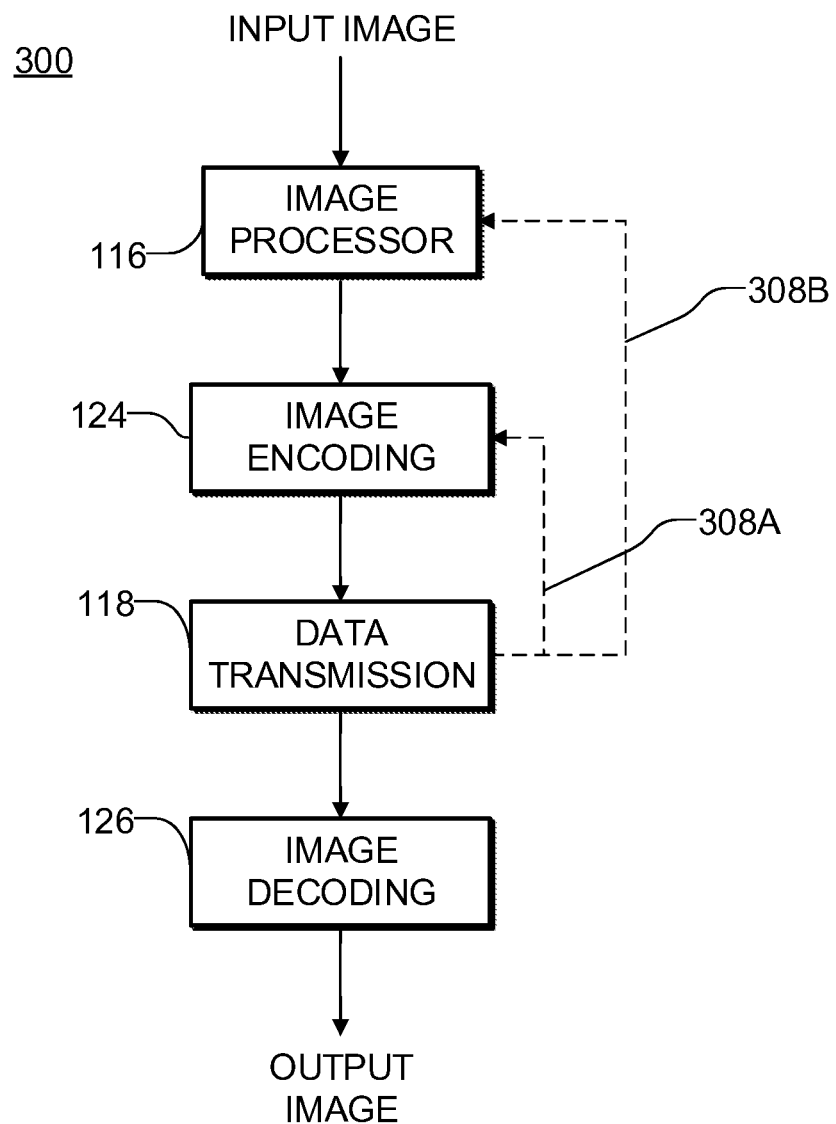
FIG. 3 is a flowchart illustrating data flows in an example combination of image processing and compression to yield a high quality, easily transmissible image according to one or more embodiments of the present disclosure.

FIG. 3 is a data flow diagram illustrating the combination of image processing and compression to yield a high quality, easily transmissible image according to one or more embodiments of the present disclosure. Input image 302 is enhanced by image processor 116 and compressed by encoder 124 to produce output image 304 which is ready for transmission to a display device 150B. The reduction of speckle noise in image processor 116 reduces the entropy of the image and improves its compressibility. Encoder 124 is able to compress the speckle-reduced image more efficiently.

FIG. 3 includes optional feedback paths 308A and 308B which, respectively, control image processor 116 and encoder 124 based on information regarding the status of data connection 118. In an example embodiment, feedback path 308A controls speckle reduction by image processor 116 based on the relationship between the volume of data to be transmitted per second and the bandwidth of the communication link(s) 118 over which the data is being transmitted (and/or an allowed bandwidth threshold set for device 150A—the allowed bandwidth threshold may be stored in a memory location accessible to image processor 116 and/or encoder 124).

In some embodiments, feedback paths 308A and/or 308B are provided by way of a control circuit (which may be implemented in hardware, configurable hardware, a processor executing machine-readable instructions or some combination thereof). The control circuit may receive as input a measure of the rate at which device 150A is generating data for transmission and may set parameters for speckle reduction and/or compression so as to transmit encoded ultrasound images having the best image quality consistent with the bandwidth available for device 150A to use for the ultrasound images. In some embodiments where the bandwidth used to transmit the encoded ultrasound images is near or at or above the applicable threshold the control circuit is configured to initially apply increased speckle-reduction. Where the bandwidth used to transmit the encoded ultrasound images remains near or at or above the applicable threshold the parameters of encoder 324 may be set to provide increased data compression.

Various techniques may be applied for speckle reduction at image processor 155. For example, Westin et. al, "Adaptive image filtering", *Handbook of medical imaging* (2000), the contents of which are incorporated herein by reference in their entirety, describes an example method for speckle noise reduction.

Figure 4:
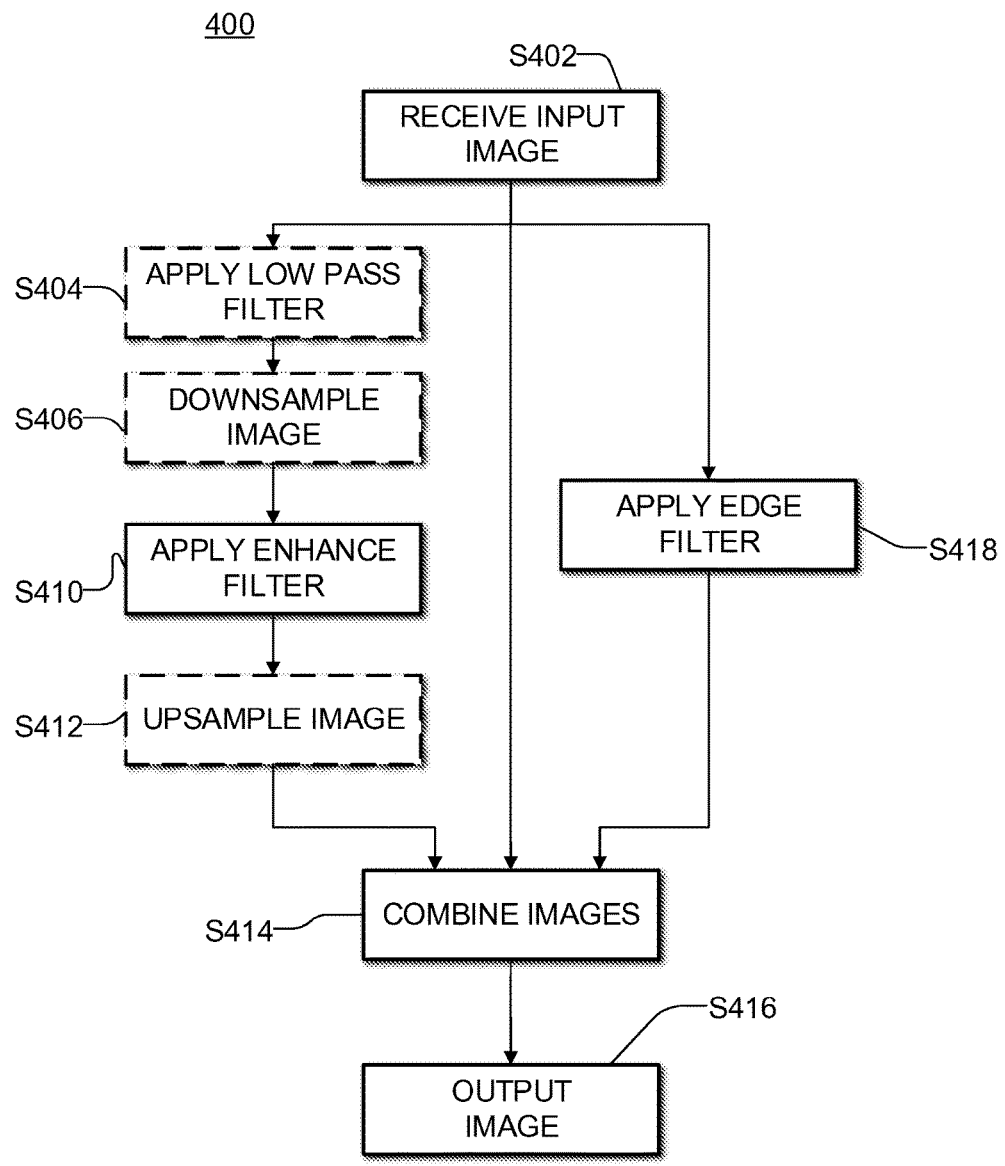
FIG. 4 is a process diagram illustrating the steps of a speckle reduction processing method according to an example embodiment of the present disclosure.

FIG. 4 is flowchart illustrating an exemplary embodiment of an adaptive image filtering technique that may be applied to reduce speckle noise implemented by image processor 155. Structural elements are identified within the image and used to adjust the filtering parameters to most effectively reduce noise while minimizing degradation of structures within the image. In some embodiments, the filtering identifies edges within the image and attempts to apply smoothing in directions that are along the edges and not across the edges.

In this exemplary embodiment, the adaptive image filtering technique comprises applying two filters in parallel and combining the outputs of these filters.

In operation S402, a log-compressed image is received from signal processor 114.

In operation S410, an enhance filter is applied to the image. The enhance filter may comprise a structure-preserving smoothing filter. One example embodiment is described in detail below. It is generally desirable to low-pass filter the image before or as part of applying the enhance filter. In some embodiments, the computational expense of applying the enhance filter is reduced by applying the enhance filter to a downsampled version of the image. Since downsampling inherently provides a certain degree of low-pass filtering, in some such embodiments the downsampling provides the requisite low-pass filtering.

FIG. 4 shows an optional low-pass filtering operation S404. FIG. 4 also shows an optional downsampling operation S406. Optionally either one or both of operations S404 and S406 is performed.

In optional operation S406 the image is down sampled. A typical scaling factor for downsampling is 50%. In some embodiments the downsampling scales each dimension by a reduction factor in the range of 20% to 70%. The image is typically scaled before the enhancement process. This may reduce computational expense and improve performance. The scaling may be predetermined or may be changed by the user or in response to another step of the processing chain. For example, the scaling factor may be decreased (thereby increasing the amount of downsampling) in order to shorten processing time and/or achieve a higher framerate.

In one example embodiment, downsampling is parameterized so that any of a number of different pre-determined down-scaling filters can be applied by adjusting a single parameter. For example, the single parameter may be a Filter ID. In some embodiments feedback path 308A comprises adjusting or selecting the amount of downsampling performed by operation S406.

If the image was downsampled in operation S406, then in operation S412, the enhanced image produced in operation S410 is upsampled to the original size.

In operation S418, an edge filter is applied to a copy of the image. The edge filter enhances edges in the image.

In operation S414 the image output by the enhance filter is combined in a weighted sum with the original image and an edge-filtered image yielded by operation S418. The weighting between the three images may be pre-determined. In one embodiment, the weighting may be 75% on the enhance-filtered image and 25% on the edge-filtered image. The resulting combined image may then be blended with the original image at a weighting of, for example, 50-60% for the combined image and 40-50% for the original image.

In operation S416, the enhanced image is output to compressor 124.

Figure 5:
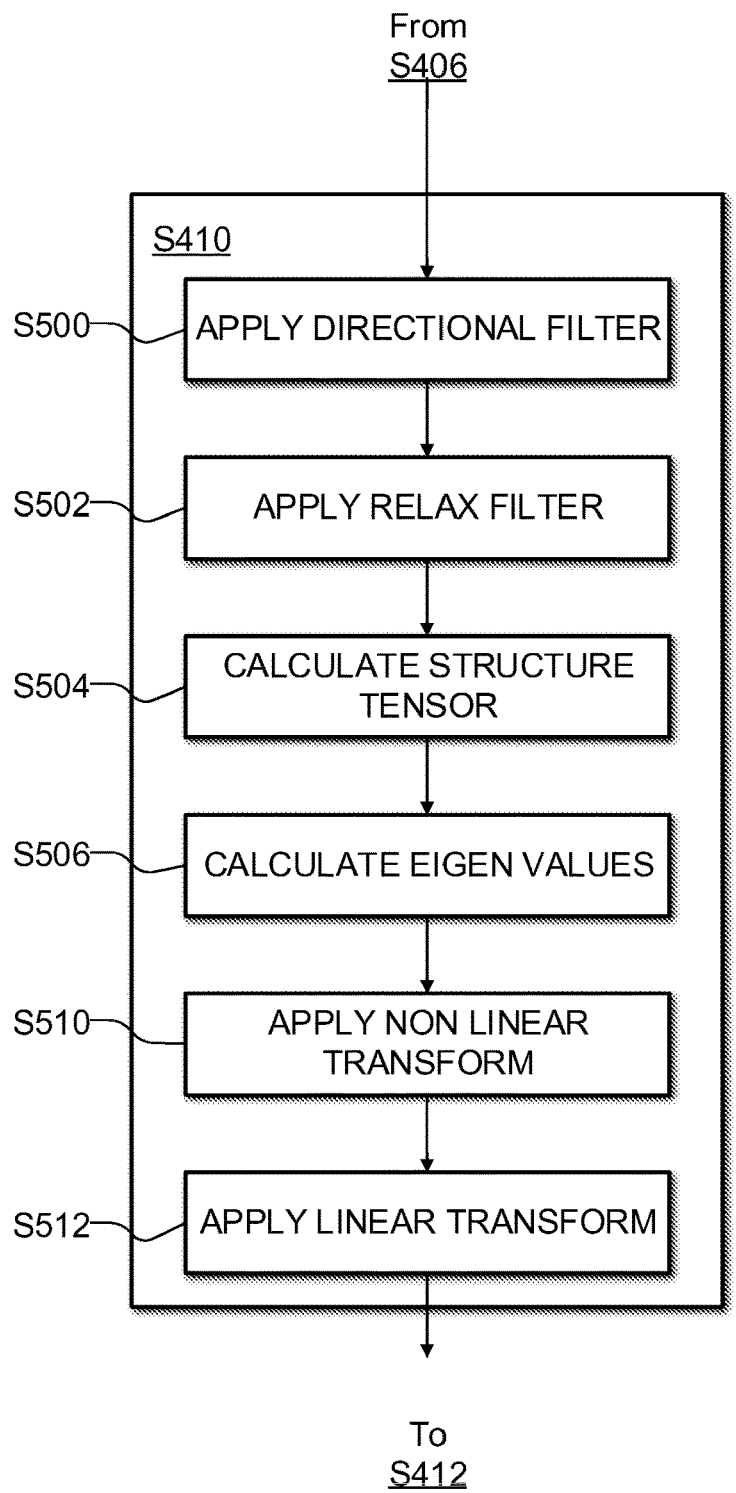
FIG. 5 is a process diagram illustrating the steps of an enhance filter for speckle reduction by an anisotropic adaptive filtering process according to an example embodiment of the present disclosure.

FIG. 5 is a flowchart illustrating an example embodiment of the enhance filter in operation S410 of FIG. 4. In this example, the enhance filter comprises an anisotropic adaptive filter. A discussion on these types of filters can be found in *The General Flow-Adaptive Filter: With Applications to Ultrasound Image Sequences* by Are Fritz Charles Jensen which is hereby incorporated herein by reference for all purposes. The filter is spatially variable, meaning its operation varies depending on the location in the image. The behavior of the filter is adjusted based on local structure information obtained from the image. The local structure information is obtained by using a structure tensor.

In operation S500, a set of directional images are generated using a set of quadrature filters. The quadrature filters are complex directional filters. It can be convenient to generate the quadrature filters in the frequency domain and to transform them into the spatial domain.

The quadrature filters each perform filtering in a different direction. In one embodiment, four quadrature filters are used with angles corresponding to 0°, 45°, 90°, and 135°. The quadrature filters may be implemented, for example, in a fashion like that disclosed by G. Granlund et al in *Signal Processing for Computer Vision*, Kluwer Academic Publishers (1995) which is hereby incorporated herein by reference for all purposes. Each directional filter yields as output a corresponding directional image having pixel values q(i,j).

In operation S502, each directional image is smoothed with a relax filter. The purpose of the relax filter is to help stabilize the directional behavior of the directional filter. For example a Gaussian filter may be used for the relax filter.

In operation 504, a local structure tensor that describes local image structure is generated using the relaxed directional images. The structure tensor, S, may be generated, for example, by linearly summing the magnitudes of the quadrature filter responses:

$$S = \sum_{k=1}^{4} q_k M_k$$

Where $q_k$ is the magnitude response of quadrature filter k and $M_k$ is the corresponding predetermined filter tensor. The structure tensor quantifies not only the dominant orientations of image structures but also the uncertainty associated with these orientations.

In operation S506, eigenvalues $\lambda_1$ and $\lambda_2$ are calculated from the directional images for each pixel. This may be done, for example using the following equations. The image pixel indices, e.g., i and j of q(i,j) are omitted for clarity.

$$\lambda_1 = \frac{1}{4}(|q_1| + |q_2| + |q_3| + |q_4|) + \frac{1}{2}\left(\sqrt{(|q_1| - |q_3|)^2 + (|q_2| - |q_4|)^2}\right)$$

$$\lambda_2 = \frac{1}{4}(|q_1| + |q_2| + |q_3| + |q_4|) - \frac{1}{2}\left(\sqrt{(|q_1| - |q_3|)^2 + (|q_2| - |q_4|)^2}\right)$$

The eigenvalues are ordered so that $\lambda_1 \geq \lambda_2 \geq 0$.

In operation S510, a control tensor is generated by normalizing and remapping the structural tensor. In some embodiments the transform between the structural tensor and the control tensor is non-linear. In some embodiments, the eigenvalues are used in the nonlinear transform.

$$C = f(S)$$

In an example embodiment the control tensor is given by:

$$C = \lambda_1/(\lambda_1^2 + \alpha^2) \times S,$$

where $\alpha$ is a resolution parameter. Carl-Fredrik Westin et al., *Adaptive Image Filtering in Handbook of Medical Imaging*, editor Isaac Bankman, Academic Press, 2000 which is hereby incorporated herein by reference for all purposes describes example ways to generate a normalized control tensor C.

In operation S512, the final enhanced image is produced by a summation of low-pass filter and weighted high-pass or all-pass filter responses. The high-pass filters, $f_{hp}$, may be fixed, spherically separable high-pass filters directed along the same orientations as the quadrature filters. The low-pass filter, $f_{lp}$, may be a fixed filter.

The high-pass or all-pass filter may be constructed from the eigenvalues and eigenvectors of the control tensor. For example, the final enhanced image may be produced according to:

$$f = f_{lp} + \sum_{k=1}^{4} C \cdot M_k f_{hp,k}$$

Where $f_{hp}$ is the output of the high pass or all pass filter, $f_{lp}$ is the output of the low pass filter, C is the control tensor, and $M_k$ are the predetermined filter tensors.

Once the enhanced image is complete, it is upsampled, if necessary, in operation S412 and then combined with the other images in operation S414.

After image enhancement, the image is compressed in order to facilitate transmission over communication link 118.

Any of a wide range of image compression algorithms may be used. MPEG and JPEG are two examples of suitable image compression techniques that may be performed by an encoder (e.g. 324) prior to transmission of the image data. The compression quality may be predetermined through trial and error or may be adjustable by the user or through feedback through another system. For example, the compression quality may be automatically decreased based on decreased network throughput or increased dropped packets. In some embodiments, feedback path 308B adjusts a compression quality parameter.

Figure 6:
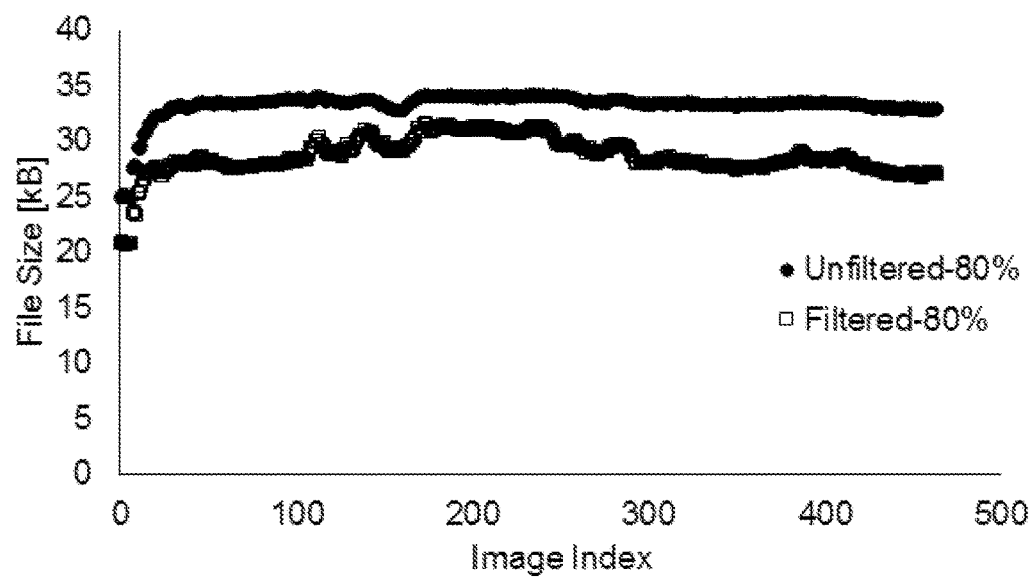
FIG. 6 is a plot depicting experimental results of speckle reduction processing according to an example embodiment of the present disclosure.

FIG. 6 is a graph depicting experimental results for the size of ultrasound images acquired from an imaging sequence of the abdomen. The graph shows how applying speckle reduction improves the compressibility of the images and results in smaller file sizes.

Figure 7:
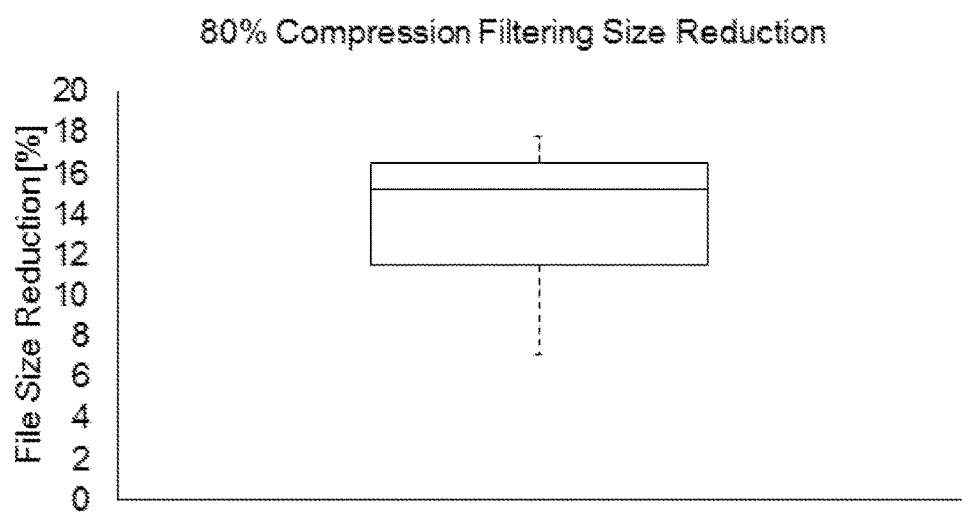
FIG. 7 is a histogram depicting the file size reduction of an ultrasound sequence with and without speckle reduction applied.

FIG. 7 is a histogram depicting the fractional decrease in file size after speckle reduction filtering for the data presented in FIG. 6.

Figure 8:
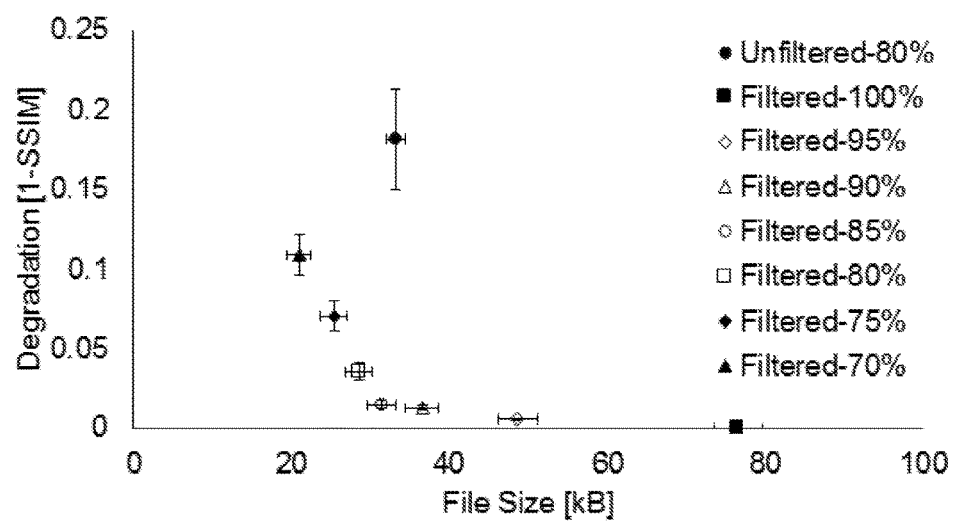
FIG. 8 is a set of plots of the structural similarity index metric for different JPEG image compression qualities.

FIG. 8 illustrates a comparison of the structural similarity index metric for the experimental image sequence using several different compression qualities. The structural similarity metric is a quantitative image quality metric based on luminance, contrast, and structure. The uncompressed filtered ultrasound image was used as a reference.

Figures 9A, 9B, 9C, 9D:
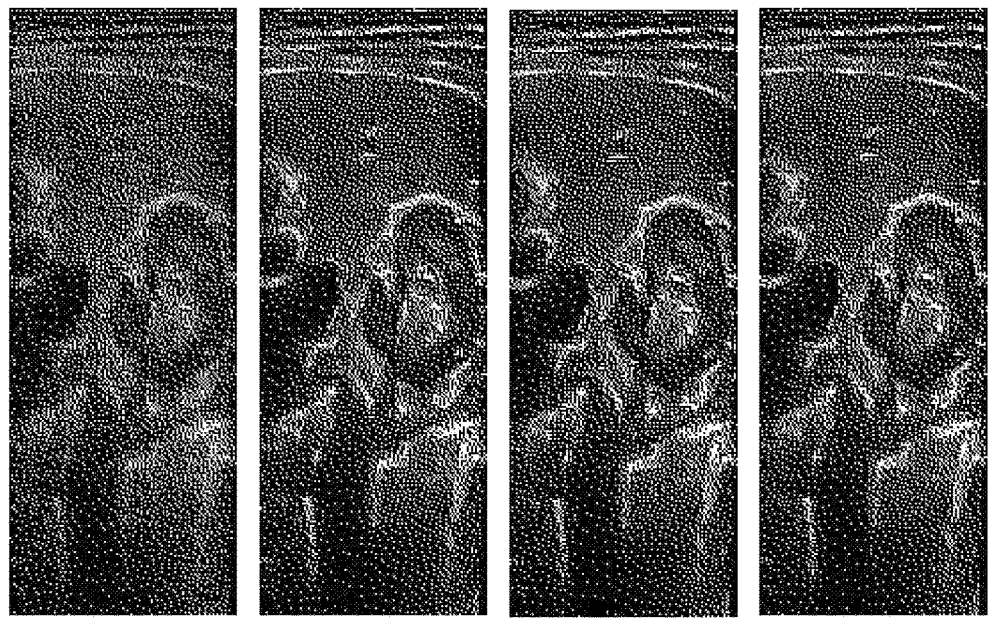
FIG. 9A is an example of an ultrasound image in its original state.
FIGS. 9B to 9D show the image of FIG. 9A with speckle reduction applied with various levels of compression quality.

FIG. 9A shows an example ultrasound image in its original form. FIGS. 9B to 9D show the same image with speckle reduction applied in addition to compression at several different qualities. In this example, FIG. 9B is the compressed at 100%, FIG. 9C is compressed at 95% and FIG. 9D is compressed at 81%.

By effectively applying advanced speckle reduction techniques suitable for limited processing power, speckle noise is reduced while maintaining structural detail, yielding high quality images. The reduction in noise also improves the compressibility, enabling high quality images to effectively be transmitted and displayed to the clinician over relatively low-bandwidth or low quality connections.

Example Usage

In one example embodiment, the image enhancement and compression process may be parameterized to easily accommodate different sets of parameters for different scanning situations. Pre-determined sets of parameters defined in conjunction with different imaging presets corresponding to different anatomies, probes, and patient types may simplify the number of adjustments required by the user.

For example, a number of parameters may be defined in a human-readable script to define each part of the image enhancement process.

In an example application an ultrasound image is made up of 128 to 1024 scan lines each having 256 to 2048 pixels. Each pixel may have a grey level specified by one byte (256 possible values) such that the raw image has a size in the range of 32 kilobytes to 2 megabytes (neglecting overhead such as an image header). It is generally desirable to obtain and display such images at a rate that provides live video that appears to provide smooth motion (e.g. at a rate of at least 20 Hz). It is often desirable, for example, to acquire and display the ultrasound images at a rate in the range of 24 to 50 Hz. For the example above, transmitting the raw ultrasound images at this rate would require a bandwidth of at least 24×32 k=786 kilobytes/sec. To transmit 1024 by 2048 pixel ultrasound images at a rate of 50/second would require a bandwidth of 100 megabytes of ultrasound data/sec.

Wireless data transmission protocols generally divide a data payload up into blocks. The blocks are transmitted in data frames that include headers, error correction bits and possibly other data. Thus, transmitting a given volume of ultrasound image data requires transmitting a larger amount of data when the overhead associated with the data communication channel is included.

Fortunately it is possible to compress image data such that a given image can be transmitted using less data. Video data compression may be lossless or lossy. Lossless data compression techniques can typically yield compressed images that are at most a factor of 2 or 3 smaller than the raw image data. Lossy techniques can produce much greater compression e.g. reduction of data volumes in the range of 20 to 200 are possible. However, higher levels of compression can cause artifacts in reconstructed images. Such artifacts can be unacceptable in medical ultrasound applications as they can obscure diagnostically significant aspects of the image.

Most lossy compression algorithms include a quality parameter that may be adjusted to increase the level of compression at the cost of reduced fidelity of the reconstructed image or to decrease the level of compression and preserve higher fidelity of the reconstructed image to the original image. Performing speckle reduction in advance of compression can yield smaller compressed image files (more compression) at the same value of the quality parameter. For example, FIG. 9 shows that performing such speckle reduction can yield compressed image data files that are more than 14% smaller than the original image data for approximately half of the video frames processed.

The ability to reduce data size while preserving image quality may be applied to reduce bandwidth required for transmission of ultrasound data from apparatus 150A to 150B and/or to increase one or more of frame rate and compression quality setting while keeping within an allocated bandwidth. The ability to reduce data size while preserving image quality may also or in the alternative be applied to increasing greyscale bit depth and/or increasing the number of pixels in the ultrasound image while keeping within an allocated bandwidth.

In an example embodiment, data communication link 118 has a usable capacity of 24 megabytes/sec. However, data communication link is a wireless link in this example and each device 150A is allocated a bandwidth of 5 megabytes/sec since several devices 150A may be in use in the same area at the same time. Applying compression to the ultrasound image data generated at apparatus 150 results in a bit rate of 5.2 megabytes/sec. However, applying both speckle reduction and compression reduces this by an average of 8% to 4.8 megabytes/sec which is within the allocated bandwidth.

In another example embodiment, apparatus 150A automatically increases the quality parameter of the encoding performed by encoder 154 to bring the average bit rate closer to but still not exceeding the allocated bit rate of 5 megabytes/second.

In another example embodiment, apparatus 150A is configured to set a bandwidth for transmission of ultrasound data to apparatus 150B. To establish a set bandwidth, apparatus 150A may determine an available bandwidth. The available bandwidth may be determined by a combination of testing data communication link 118 to determine what bandwidth it can sustain and looking up a stored bandwidth parameter (which may depend on parameters affecting the acquisition of ultrasound images by apparatus 150A—for example, ultrasound acquisition settings which specify larger (more pixels and/or more bit depth) ultrasound images and/or higher frame rates may be set to use more bandwidth, if available, than ultrasound acquisition settings which specify smaller ultrasound images and/or lower frame rates). In some embodiments controller 110 is configured to look up a stored bandwidth parameter (optionally selecting the parameter based on current ultrasound acquisition settings). The stored bandwidth parameter sets a maximum bandwidth. Controller 110 may also be configured to test the reliable bandwidth of data communication link 118, for example by sending test data to apparatus 150B. If the maximum reliable bandwidth of data communication link 118 is less than the maximum bandwidth then controller 110 makes the set bandwidth equal to the maximum reliable bandwidth. Otherwise controller 110 may set the set bandwidth equal to the maximum bandwidth.

Controller 110 may check to determine whether or not the bandwidth required to transmit the ultrasound image data exceeds the set bandwidth. If so, controller 110 may automatically adjust parameters to reduce the required bandwidth. For example, controller 110 may increase a degree of speckle-reduction filtering and/or reduce one or more of ultrasound frame rate and compression image quality to bring the required bandwidth within the set bandwidth.

As ultrasound data is being transmitted from apparatus 150A to apparatus 150B, controller 110 may continue to monitor the bandwidth required by the ultrasound data. This may change, for example, as a result of different image content in the ultrasound images. Controller 110 may adjust the above parameters in real time to keep the bandwidth being used to transmit the ultrasound image data within the current set bandwidth.

Controller 110 may optionally monitor the maximum reliable bandwidth and re-establish the set bandwidth from time to time in case the maximum reliable bandwidth is less than the current set bandwidth or the current set bandwidth is less than both the maximum bandwidth and the maximum reliable bandwidth.

In any of the above embodiments device 150A may optionally transmit to device 150B data indicating what speckle-reduction, if any, has been applied to the ultrasound images by device 150A. In some such embodiments device 150B comprises speckle reduction filters (that may be the same or different from the speckle reduction filters provided at device 150A). In some embodiments device 150B is configured to automatically apply speckle-reduction filtering where speckle reduction filtering was not performed at device 150A. Shifting the computational burden of speckle-reduction filtering from device 150A to device 150B in cases where there is sufficient bandwidth to transmit the generated images without speckle reduction in may help to conserve power at device 150A.

Interpretation of Terms

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

One byte is 8 bits. One kilobyte is 1024 bytes. One megabyte is $2^{20}$ bytes.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different described embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for obtaining and displaying ultrasound images, the method comprising:
   transmitting ultrasound signals into a volume of interest and receiving echo signals from within the volume of interest;
   beamforming the echo signals to yield an original ultrasound image;
   performing speckle reduction on the original ultrasound image;
   compressing the speckle-reduced ultrasound image, wherein compression of the speckle-reduced ultrasound image produces a compressed speckle-reduced ultrasound image with: an improved image quality or a reduced size, over a comparable compression of the original ultrasound image, and wherein an intensity of the performed speckle reduction is controlled to maintain a bandwidth required for transmission of the compressed speckled-reduced ultrasound image below a bandwidth of a data communication link to a display device;

transmitting the compressed speckle-reduced ultrasound image over the data communication link to the display device;

at the display device, decompressing and scan converting the compressed speckle-reduced ultrasound image; and displaying the decompressed and scan-converted speckle-reduced ultrasound image on a display of the display device.

2. A method according to claim 1 wherein performing the speckle reduction on the original ultrasound image comprises applying an adaptive filter to the original ultrasound image.

3. A method according to claim 2 wherein applying the adaptive filter comprises applying a plurality of directional filters to the original ultrasound image to yield corresponding directional images and processing pixel values for the directional images to yield a control tensor and eigenvalues for the control tensor.

4. A method according to claim 2 wherein performing speckle reduction on the original ultrasound image further comprises downsampling the ultrasound image data prior to applying the adaptive filter and upsampling an output of the adaptive filter.

5. A method according to claim 4 wherein downsampling comprising downsampling by at least a factor of two in each dimension.

6. A method according to claim 4 wherein performing the speckle reduction further comprises applying a smoothing filter prior to upsampling the filtered images.

7. A method according to claim 6 wherein performing the speckle reduction further comprises applying an edge preservation filter prior to upsampling the filtered images.

8. A method according to claim 6 wherein performing the speckle reduction further comprises combining the filtered upsampled images with the original ultrasound image.

9. A method according to claim 8 wherein combining the filtered upsampled image with the original ultrasound image comprises making a weighted sum of the filtered upsampled image and the original ultrasound image.

10. A method according to claim 4 wherein an amount of the downsampling is determined at least in part based on a bandwidth threshold for the transmitting of the compressed speckle-reduced ultrasound image and the bandwidth being used for transmitting compressed speckle-reduced ultrasound images.

11. A method according to claim 1 wherein the original ultrasound image has a size of at least 12288 pixels and a bit depth of at least 8 bits.

12. A method according to claim 11 comprising repeating the method at a frame rate of at least 20 frames per second.

13. A method according to claim 12 wherein the bandwidth of the data communication link does not exceed 20 megabytes/second.

14. A method according to claim 1 comprising controlling both a quality level of the image compression and the intensity of speckle-reduction to maintain the bandwidth required for transmission of the transmitted compressed speckle-reduced ultrasound images below the bandwidth of the data communication link.

15. A method according to claim 1 comprising adjusting a frame rate to maintain the bandwidth required for transmission of the transmitted compressed speckle-reduced ultrasound images below the bandwidth of the data communication link.

16. An ultrasound imaging system comprising an ultrasound imaging machine and a display device, wherein the ultrasound imaging machine comprises:
a transducer for transmitting ultrasound signals into a volume of interest and receiving echo signals from within the volume of interest;
a receiver for beamforming the echo signals, the echo signals for yielding an original ultrasound image;
an image processor for performing speckle reduction on the original ultrasound image;
an encoder for compressing the speckle-reduced ultrasound image, wherein compression of the speckle-reduced ultrasound image produces a compressed speckle-reduced ultrasound image with: an improved image quality or a reduced size, over a comparable compression of the original ultrasound image, and wherein an intensity of the speckle reduction performed by the image processor is controlled to maintain a bandwidth required for transmission of the compressed speckled-reduced ultrasound image below a bandwidth of a data communication link to the display device; and
a communication interface for transmitting the compressed speckle-reduced ultrasound image over the data communication link to the display device; and wherein the display device comprises:
a decoder for decompressing the transmitted, compressed speckle-reduced ultrasound image, and
a scan converter for scan converting the decompressed speckle-reduced ultrasound image, so that the scan-converted, decompressed speckle-reduced ultrasound image is displayed at the display device.

17. The ultrasound imaging system of claim 16, wherein when performing the speckle reduction on the ultrasound image, the image processor applies an adaptive filter to the ultrasound image.

18. The ultrasound imaging system of claim 16, wherein the image processor controls both a quality level of the image compression and the intensity of speckle-reduction to maintain the bandwidth required for transmission of the transmitted compressed speckle-reduced ultrasound images below the bandwidth of the data communication link.

19. The ultrasound imaging system of claim 16, wherein the image processor adjusts a frame rate to maintain the bandwidth required for transmission of the transmitted compressed speckle-reduced ultrasound images below the bandwidth of the data communication link.

* * * * *